(12) United States Patent
Brenne et al.

(10) Patent No.: US 11,022,595 B2
(45) Date of Patent: Jun. 1, 2021

(54) DETERMINING THE PHASE COMPOSITION OF A FLUID FLOW

(71) Applicant: STATOIL PETROLEUM AS, Stavanger (NO)

(72) Inventors: Lars Brenne, Sandnes (NO); Svend Tarald Kibsgaard, Porsgrunn (NO); Bjarne Monsen, Røyneberg (NO); Tom Odin Gaustad, Korsvegen (NO)

(73) Assignee: STATOIL PETROLEUM AS, Stavanger (NO)

( * ) Notice: Subject to any disclaimer, the term of this patent is extended or adjusted under 35 U.S.C. 154(b) by 289 days.

(21) Appl. No.: 15/738,944

(22) PCT Filed: Jun. 26, 2015

(86) PCT No.: PCT/EP2015/064607
§ 371 (c)(1),
(2) Date: Dec. 21, 2017

(87) PCT Pub. No.: WO2016/206761
PCT Pub. Date: Dec. 29, 2016

(65) Prior Publication Data
US 2018/0188226 A1 Jul. 5, 2018

(51) Int. Cl.
*G01N 33/28* (2006.01)
*F04D 31/00* (2006.01)
(Continued)

(52) U.S. Cl.
CPC ......... *G01N 33/2823* (2013.01); *F04D 13/08* (2013.01); *F04D 25/0686* (2013.01);
(Continued)

(58) Field of Classification Search
CPC .... G01N 33/2823; G01N 27/00; G01N 25/00; F04D 13/08; F04D 25/0686; F04D 27/001; F04D 27/02; F04D 31/00; F01N 33/2823

See application file for complete search history.

(56) References Cited

U.S. PATENT DOCUMENTS 6,591,201 B1 * 7/2003 Hyde ................. G01F 25/0007
700/281
10,018,020 B2 * 7/2018 Phillippi ................ F04D 13/12
(Continued)

FOREIGN PATENT DOCUMENTS

EP         2 325 494 A1    5/2011
WO    WO 2009/131462 A2   10/2009
(Continued)

OTHER PUBLICATIONS

International Search Report, issued in PCT/EP2015/064607, dated Dec. 3, 2015.
(Continued)

*Primary Examiner* — Bryan Bui
(74) *Attorney, Agent, or Firm* — Birch, Stewart, Kolasch & Birch LLP (57) ABSTRACT

A method of identifying the phase composition and/or changes in the phase composition of a fluid flowing through a turbomachine includes monitoring changes in at least one electrical parameter associated with operation of the turbomachine, and employing a known correlation between phase composition and or phase composition changes, and changes in the electrical parameter(s) to associate the monitored changes with changes in the actual phase composition of the fluid.

19 Claims, 6 Drawing Sheets

(51) Int. Cl.
*F04D 13/08* (2006.01)
*F04D 25/06* (2006.01)
*F04D 27/00* (2006.01)
*F04D 27/02* (2006.01)
*G01N 25/00* (2006.01)
*G01N 27/00* (2006.01)
*F04D 13/10* (2006.01)

(52) U.S. Cl.
CPC ........... *F04D 27/001* (2013.01); *F04D 27/02* (2013.01); *F04D 31/00* (2013.01); *G01N 25/00* (2013.01); *G01N 27/00* (2013.01); *F04D 13/10* (2013.01); *F05D 2210/10* (2013.01); *F05D 2210/13* (2013.01); *F05D 2260/80* (2013.01)

(56) References Cited

U.S. PATENT DOCUMENTS

| | | |
|---|---|---|
| 2012/0224980 A1 | 9/2012 | Uptigrove |
| 2017/0089192 A1* | 3/2017 | Rendusara ............. F04D 13/10 |

FOREIGN PATENT DOCUMENTS

| | | |
|---|---|---|
| WO | WO 2012/007553 A1 | 1/2012 |
| WO | WO 2015/043915 A1 | 4/2015 |

OTHER PUBLICATIONS

Written Opinion of the International Searching Authority, issued in PCT/EP2015/054607, dated Dec. 3, 2015.

* cited by examiner

DETERMINING THE PHASE COMPOSITION OF A FLUID FLOW

TECHNICAL FIELD

The present invention relates to determining the phase composition of a fluid flow through a turbomachine such as a turbine, compressor or pump.

BACKGROUND

Turbomachines are machines which transfer energy between a rotor and a fluid. Turbomachines such as compressors and pumps are used for pressurising fluids, whilst turbines are used to transfer energy from the fluid to the rotor, e.g. for the purpose of generating electricity. In the oil and gas industry, fluid produced from a well may be compressed or pumped using turbomachinery in order to help transport the fluid to another location far away from the well. Turbomachines can be very important in extending the life of a hydrocarbon-well beyond the point in time when the pressure available from the formation falls below that required to produce unassisted. A turbomachine may be used to lower the pressure towards the reservoir, effectively sucking hydrocarbons out of the formation, and then providing pressurised fluid on the delivery (output) side. Exemplary turbomachine for use in hydrocarbon production are described in WO2009/131462 and WO2012/007553.

Fluid from a hydrocarbon producing well may typically be a "multiphase" fluid containing both gas and liquid phase components in some proportion. Traditional compressors and pumps are designed to pressurise single-phase gas and liquid respectively. In the event of an undesirable operation of a process plant, liquid may be carried with the gas into the compressor and similarly gas may enter the pump. Presence of liquid in the gas being pressurised by the compressor may lead to fouling, that may in turn impact the rotor-dynamic behaviour and the machine's ability to produce a pressure increase. Similarly, the presence of gas from cavitation or from the process may reduce pump performance.

In recent years compression and pumping machinery has also been developed where the process fluid may consist of a mixture of gas and liquid. It is important with such machinery to know the mixing ratio of the gas and liquid phase to ensure protection and correct operation of the facility.

It is desirable to be able to monitor the phase composition of a fluid flowing through a turbomachine, i.e. the relative proportions of liquid and gas. More particularly, it is desirable to be able to monitor changes in that phase composition, for example in order to be able to control downstream plant to achieve a better single-phase fluid flow. Traditional approaches to achieve this utilise a flow device located in the turbomachine inlet or outlet. An example of such a flow device is the multiphase flow meter which uses a combination of measurements including temperature and pressure, and measurements obtained using a nuclear source. However, such known methods have the disadvantage that they add complexity that impacts the availability and cost of the total system.

SUMMARY OF THE INVENTION

The aim of this invention is to analyse available signals such as, but not limited to, motor current, bearing forces, shaft position, shaft rotating speed, and/or motor slip to determine for example:

if gas is present within a continuous liquid phase and to quantify the amount of gas dispersed into the liquid phase;

if liquid is present within a continuous gas phase and to quantify the amount of liquid entrained into the gas phase.

According to a first aspect of the present invention there is provided a method of identifying the phase composition and/or changes in the phase composition of a fluid flowing through a turbomachine. The method comprises the steps of (a) monitoring changes in at least one electrical parameter associated with operation of the turbomachine, and (b) employing a known correlation between phase composition and or phase composition changes, and changes in the electrical parameter(s) to associate the monitored changes with changes in the actual phase composition of the fluid.

It will be appreciated that the expression "phase composition" is used to indicate the relative proportions of the phases present in the fluid, e.g. liquid and gas, as well as, optionally, the identities of the phases present in the fluid.

The electrical parameter may be a parameter of an electrical power supply used to drive a motor of the turbocompressor, for example the current, voltage or power of the power supply. The electrical power supply may be controlled by a frequency converter or a fixed power grid frequency. The method may further comprise configuring said frequency converter or a fixed power grid frequency to maintain a substantially constant motor speed or fluid compression level.

Alternatively, the parameter may be a parameter of a sensed electrical signal or of a control signal, for example a parameter of a control signal used to stabilise the turbomachine.

The step of monitoring changes in at least one electrical parameter associated with operation of the turbomachine may comprise monitoring changes in the absolute value of said parameter.

The step of monitoring changes in at least one electrical parameter associated with operation of the turbomachine may comprise monitoring changes in a deviation of said parameter, for example changes in the standard deviation of the parameter. The method may further comprise sampling the deviation of the electrical parameter at each of successive sampling windows.

The changes in the phase composition may be changes in the liquid fraction of a fluid containing liquid and gas. The method may comprise using the identified changes in the liquid fraction to detect liquid slugs in the fluid.

The present invention is applicable in particular, though not necessarily, to the case where said fluid comprises hydrocarbons flowing from a production well, and the turbomachine is provided at a subsea location.

The method may further comprise introducing a component upstream of an inlet of the turbomachine in order to cause fluctuations of an undesired phase of the fluid.

According to a second aspect of the present invention there is provided a method of controlling a valve associated with a turbomachine and comprising using the method of the above first aspect to identify changes in the phase composition of a fluid flowing through the turbomachine, and controlling said valve in dependence upon identified changes.

According to a third aspect of the present invention there is provided a method of detecting a faulty operation of a turbomachine, the method comprising identifying changes in the phase composition of a fluid flowing through a turbomachine using the method of any one of the preceding claims, and detecting changes in said at least one electrical parameter that cannot be correlated with changes in the fluid phase composition and using these changes to identify said faulty operation.

According to a fourth aspect of the present invention there is provided a monitor for monitoring changes in the phase composition of a fluid flowing through a turbomachine and comprising a detector for monitoring changes in at least one electrical parameter associated with operation of a turbomachine, and an analyser for employing a known correlation between phase composition or phase composition changes, and changes in the electrical parameter(s) to associate the monitored changes with the actual phase composition of the fluid or changes in the actual composition.

According to a fifth aspect of the present invention there is provided a computer program which, when run on a computer, causes the computer to monitor changes in at least one electrical parameter associated with a turbomachine, and employ a known correlation between phase composition or changes in the phase composition, and changes in the electrical parameter(s) to associate the monitored changes with the actual phase composition of a fluid, or changes in the actual fluid composition, flowing through the turbomachine fluid.

According to a sixth aspect of the present invention there is provided a method of determining the composition of a liquid phase of a multiphase fluid flowing through a turbomachine, the method comprising using the method of the above first aspect to identifying the phase composition and/or changes in the phase composition of said fluid, measuring the temperature of the fluid at the fluid inlet and outlet of the turbomachine, using the difference in temperatures at the inlet and outlet, in combination with the identified phase composition and/or identified changes in phase composition, to determine the composition of the liquid phase.

According to a further aspect of the present invention there is provided a method of determining make up of a liquid phase flowing through a turbomachine. This takes into consideration that, where the primary phase is gas, the presence of liquid in the compressor is likely to cool the gas during the compression process. For an inlet temperature of 15 C, in the absence of liquid phase the outlet temperature may be expected to be around 100 C. In the presence of a liquid, the outlet temperature may be reduced to 96 C due to evaporation of the condensate/oil. However, the degree to which the outlet temperature is reduced will depend upon the nature of the liquid phase. Oil will contribute much more to cool the gas during the compression process since it will partially evaporate, while the presence of water (and or MEG (glycol) will produce only minimal cooling (some additional cooling will be effected by the gas due to the higher temperature but not to the same extent as will result from the presence of condensate/oil). By measuring the pressure and temperature at the inlet and the outlet of the machine, the actual cooling effect (removed energy) provided by the liquids can be determined. By comparing this in turn with the removed energy from a normally dry compression process, the liquid composition at the inlet may be estimated, i.e. how much is water/glycol compared to the oil/condensate.

DETAILED DESCRIPTION

An approach to determining the phase composition of a fluid flow through a turbomachine such as a compressor or pump will now be described. This approach is based upon the observation that the gas quality of a multiphase fluid determines the flow regime as described in FIG. 1 and also impacts the level of mass flow rate fluctuations in the fluid. Such mass flow rate fluctuations in the incoming fluid to the machine give rise to different levels of fluctuations in electrical signals observable in respect of the turbomachine behaviour and performance.

For a fluid, the gas mass fraction (GMF) or gas quality is defined as:

$$GMF = \frac{\dot{m}_G}{\dot{m}_G + \dot{m}_A + \dot{m}_C} = \frac{\dot{m}_G}{\dot{m}_G + \dot{m}_L} \qquad \text{[Equation]}$$

where the mass flow rates are denoted $\dot{m}_G$ for the gas phase, $\dot{m}_A$ for the aqueous phase (including, if relevant, liquids other than oil), $\dot{m}_C$ for the oil or condensate phase, and $\dot{m}_L$ for the total free liquid phase.

Similarly, a gas volume fraction (GVF), that compares the volume rate of gas with the actual pipe volume, assuming that the gas and liquid behave homogenously, is defined as.

$$GVF = \frac{\dot{Q}_G}{\dot{Q}_G + \dot{Q}_A + \dot{Q}_C} = \frac{\dot{Q}_G}{\dot{Q}_G + \dot{Q}_L} \qquad \text{[Equation 2]}$$

where Q denotes gas volume rates applying the nomenclature of Equation 1.

A superficial velocity (U) of both liquid and gas is defined as if the single fluid phase was utilising the complete pipe or available flow area (i.e. the cross-sectional area, $A_{CR}$).

$$U_{GS} = \frac{\dot{Q}_G}{A_{CR}} \qquad \text{[Equation 3]}$$

$$U_{LS} = \frac{\dot{Q}_L}{A_{CR}} \qquad \text{[Equation 4]}$$

Figure 1:
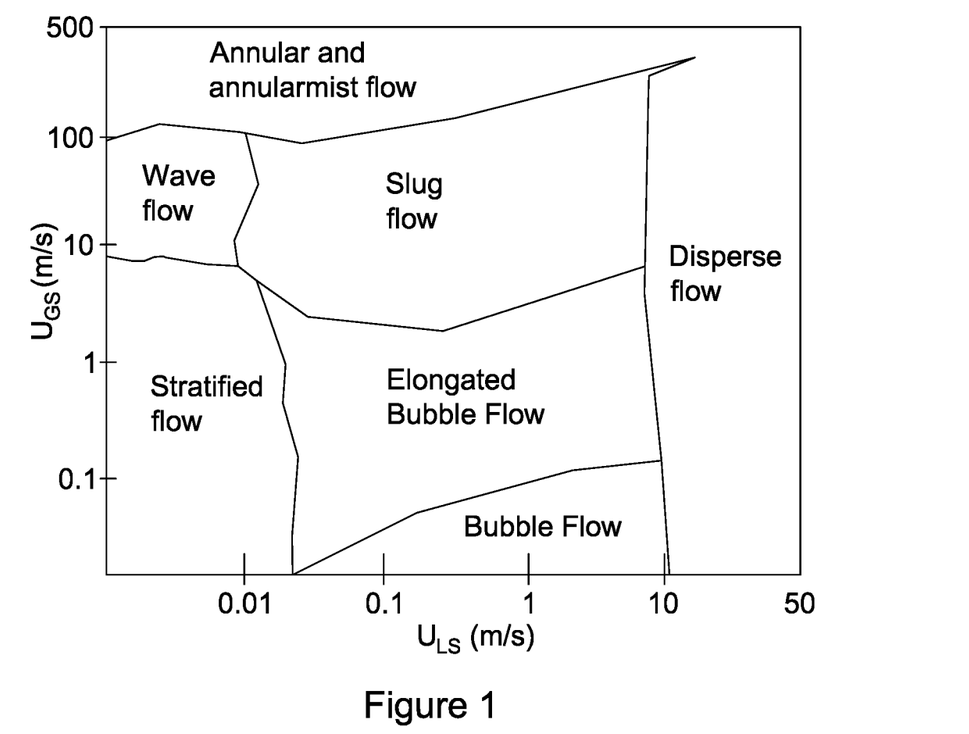
FIG. 1 illustrates multiphase fluid flow regimes or patterns that exist as a function of the mixing ratio, illustrated using exemplary gas and liquid velocities.

Different multiphase flow patterns can be described based on the actual visual behaviour of the gas-liquid mixture. FIG. 1 illustrates how different flow patterns for a gas-liquid mixture develop depending on the mixing ratio of the two phases with use of superficial velocities for the liquid (x-axis) and gas (y-axis).

The nature of multiphase flow behaviour is transient, depending on the flow regime or the mixing ratio of gas and liquid. Typically, a low fluid velocity with a large amount of liquid, gives rise to bubble or dispersed flow. Such a liquid-dominant system will normally be pressurised by using a pump, and various amounts of gas entrained into the liquid phase will impact the actual bulk density of the mixture. As the gas bubbles behave in a transient mode, the actual mass flow rate to the pump will vary.

In the case of gas-dominant systems, the liquid will be entrained as films on the walls of the system and/or will be present as a mist or entrained droplets traveling with similar velocity to the gas phase. The mass transient behaviour of such a fluid composition is increasing with the liquid content.

$$\rho_{mix} = GVF \cdot \rho_G + (1-GVF) \cdot \rho_L \quad \text{[Equation 5]}$$

where the densities applied are defined as $\rho_{mix}$, for the gas-liquid mixture (multiphase fluid), $\rho_G$ for the density of the gas, and $\rho_L$ for the bulk density of the liquid.

If one of the fluid phases in a multiphase flow behaves in a transient way, i.e. the mass flow rate changes with time, the actual mass flow rate entering the turbomachine will also change. Such a change in the mass flow rate will impact the torque required to keep a pump or compressor running with a constant speed or rotor velocity. If a frequency converter (e.g. variable speed drive—VSD) is applied towards an electric driven motor, the required torque change will be reflected in a changed motor current to maintain the same rotating speed.

Figure 2:
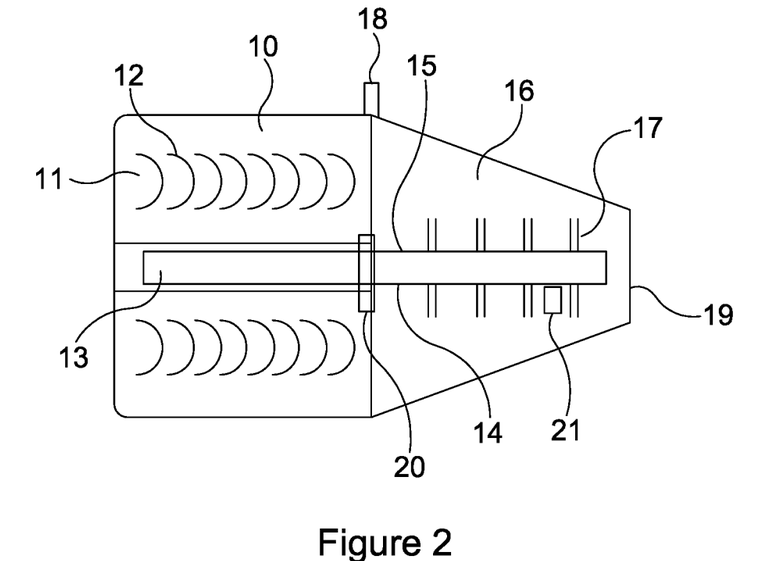
FIG. 2 illustrates schematically a typical compact compressor, with motor and compressor integrated into the same pressure casing.

FIG. 2 illustrates schematically a typical compact motor-compressor for use in subsea hydrocarbon production. The motor 10 comprises a fixed stator 11 with stator windings 12, and a rotor 13. The rotor 13 is coupled to a further rotor 15 of the compressor 16. A number of impellers 17 are attached to the compressor rotor 15. The impellers are rotated by the rotor 15 in order to move fluid from a compressor inlet 18 to a compressor outlet 19. The motor and compressor rotors are kept in position by radial bearings 20 and axial bearing 22. In use, the fluid in the outlet will be at a significantly higher pressure than the fluid in the inlet.

As well as stator windings to drive the rotor, the motor and compressor may have further components to control and stabilise the rotor movement or performance. For example, the compressor may comprise means 22 to axially control the position of the rotor 15, working to overcome any excessive thrust forces from the rotor 15. The compressor may also comprise a sensor 21—that could be for instance a keyphasor—used for rotating speed measurement. Data available from sensor 21 or current from the power supply to the motor can be analysed as described in FIG. 6 to quantify the fluid composition processed by the machine.

Figure 3:
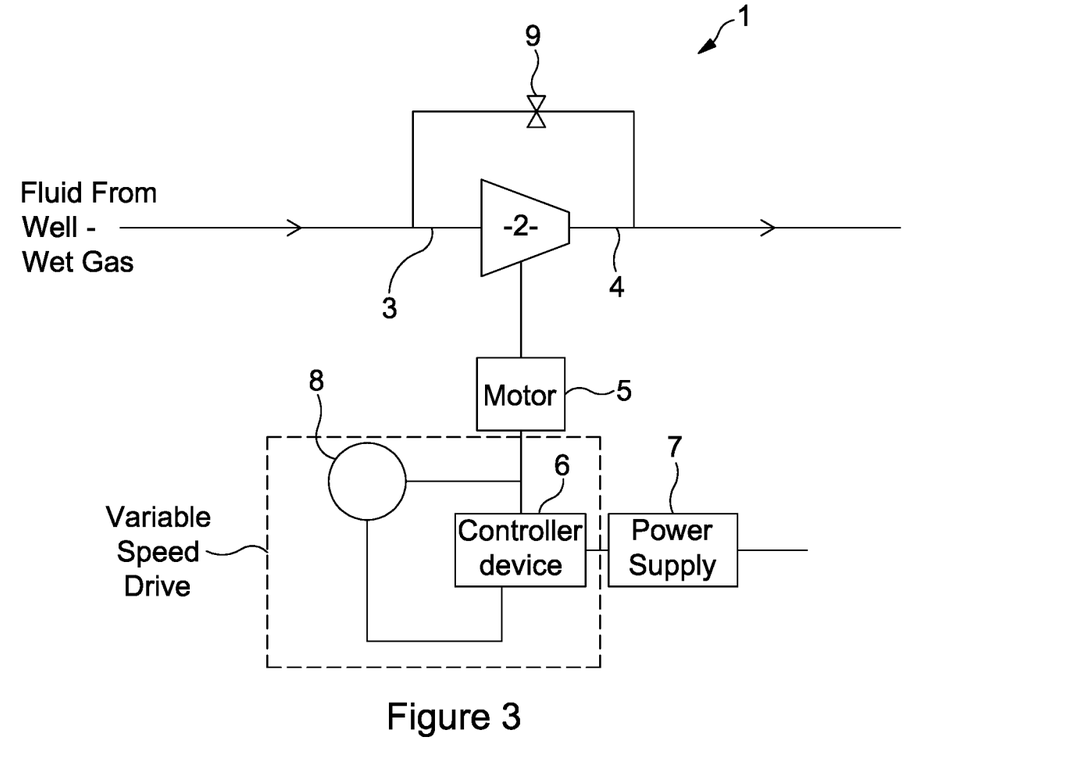
FIG. 3 illustrates schematically a system for monitoring changes in the phase composition of a fluid flow through a (frequency-converter driven) motor compressor.

In a typical electrical driven compressor system, a frequency converter (FC) may be used. For a direct coupled motor-compressor as shown in FIG. 2, the frequency converter converts a fixed supply frequency to a required motor frequency proportional to the compressor speed for a direct coupled motor-compressor shaft as shown in FIG. 2. With reference to FIG. 3, a system utilising a frequency converter comprises a compressor 2 which receives multiphase fluid from a reservoir or pipe system at an inlet 3 (although shown schematically, the motor-compressor may conform generally to the arrangement described with respect to FIG. 2). The multiphase fluid is a fluid comprising gas and liquid. The fluid passes through the compressor to an outlet 4, and the compressor acts to pressurise the fluid. The compressor has a housing in which are provided the rotatable impellers (not shown), which rotate to compress the fluid. The impellers are provided in the flow path of the fluid through the compressor housing between the inlet and the outlet. The compressor 2 is driven by an electrical motor 5 which in turn is supplied with electrical energy from an electrical power supply 7 via a controller 6. The controller 6 is arranged to control or adjust the frequency of the motor drive signal in order to achieve a desired speed. Whilst the power supply 7 and controller 6 may be collocated with the motor 5, they may also be located remotely, in some cases many tens of kilometres away.

In normal operation, the turbomachine must be able to meet the desired production rate, which means that the speed or revolutions per minute of the impellers is changed to accommodate the required outlet pressure or downstream pipe system flow resistance. The running frequency and thereby compressor pressure ratio or work can be set in the frequency converter controller. As will be appreciated, in the presence of a fluctuating fluid composition, the load on the compressor varies and the frequency controller regulates the current to meet the required torque to maintain the operating frequency or rotating speed.

As has already been discussed, liquid is typically present in the pumped fluid in small amounts for most hydrocarbon gas fields, for example up to 5% liquid content by volume. The liquid phase is dispersed in the continuous gas phase and the fluid is pressurised by transferring mechanical energy through the compressor. However, the composition of a multiphase fluid transported inside a pipe fluctuates over time, such that the amount of liquid in the fluid entering the compressor may vary.

As seen in FIG. 3, an electrical measurement device 8 is provided on the electrical supply line to the motor 5. The measurement device 8, e.g. a volt meter or amp meter, measures electrical energy parameters, namely phase current ($I_p$) and phase voltage ($V_p$), supplied by the power supply, or in this case the frequency converter, to the motor 5. [It will of course be appreciated that the measurement device 8 does not need to be located within the FC, but could be located at any appropriate point in the supply line, e.g. between the FC and the motor. The device 8 may then be coupled for example to a standalone computer that is configured to analyse the power signal.] In order to maintain a pre-set speed during operation of the compressor in the presence of a flow with varying load, the supplied current is varied correspondingly. By increasing the current, torque is increased and the compressor does more work against the load exerted by the fluid to keep the desired speed. The measured current and voltage response of the frequency converter can then be used to determine a fluid property.

More specifically, the measured motor current is proportional to the work transferred by the compressor rotor to the fluid. In turn, the work performed by the compressor can be related to the composition of the fluid, i.e. mixture of gas and liquid, through the following polytropic head equation (6) and the motor input power equation (8):

$$Y_{TP} = \frac{n_{TP}}{n_{TP}-1} \cdot \left[\frac{p_2}{\rho_{H2}} - \frac{p_1}{\rho_{H1}}\right] \quad \text{[Equation 6]}$$

where $$n_{TP} = \frac{\ln\left(\frac{p_2}{p_1}\right)}{\ln\left(\frac{\rho_{H2}}{\rho_{H1}}\right)} \quad \text{[Equation 7]}$$

and where p1 and p2 are the inlet and outlet pressures of the compressor, and $\rho_{H1}$ and $\rho_{H2}$ are the multiphase bulk densities at the compressor inlet and outlet.

$$P_w = \dot{m}_{TP} \cdot \frac{Y_{TP}}{\eta_{TP} \cdot \eta_m} \quad \text{[Equation 8]}$$

Where the $\dot{m}_{TP}$ is the multiphase fluid mass flow rate [kg/s], $Y_{TP}$ the multiphase fluid theoretical work [J/kg] defined din Equation 6, and $\eta_{TP}$ and $\eta_m$ represent the compressor and motor efficiency, respectively.

The electrical power supply (Equation 8) is equal to the fluid energy increase through the machine as shown in Equation 8, i.e.;

$$P_E \sqrt{3} \cdot U_{LL} \cdot I_{L\_RMS} \cdot \cos\varphi = P_w = \dot{m}_{TP} \cdot \frac{Y_{TP}}{\eta_{TP} \cdot \eta_m} \quad \text{[Equation 9]}$$

Where $P_E$ is the equation normally used for the power supply to a conventional three phase motor using the line to line voltage $U_{LL}$ and line current $I_{L\_RMS}$.

As can be seen from Equation 9, the compressor power is proportional to the change in mass flow rate (fluid composition) into the compressor and such transient is also proportional to the change in line current $I_{L\_RMS}$ with the same magnitude for a running frequency and thereby line to line voltage $U_{LL}$ kept constant. Accordingly, supposing liquid and gas fractions are present in the inlet, and the liquid fraction increases, then the mass flow rate and the bulk density are increased. As the equation indicates, the work of the compressor then increases. The motor current needed to handle the fluid with the changed density at the same level of compression is then likewise affected. By performing an analysis of the electric current, the composition of the fluid flow can be determined.

The control of an anti-surge valve 9 can be achieved using the determined fluid property when necessary. For example, where a significant decrease in the liquid content is identified, the anti-surge valve may be actuated to allow fluid to flow from the outlet of the compressor to the inlet in order to prevent surge in the compressor. Control of an anti-surge valve using a known multi-phase meter is described in WO2012/007553.

A software algorithm may be used to analyse the sinusoidal motor current from the frequency converter. A root mean square (RMS) of the current is obtained and stored for each sinusoidal period: if the motor operates at 120 Hz, 120 data points are collected for each given consecutive sample window. The standard deviation of the 120 points for each sample window is obtained. The result is a continuous measure of the actual fluctuating level of the motor drive current. This is described further below with reference to FIG. 5.

Figure 4:
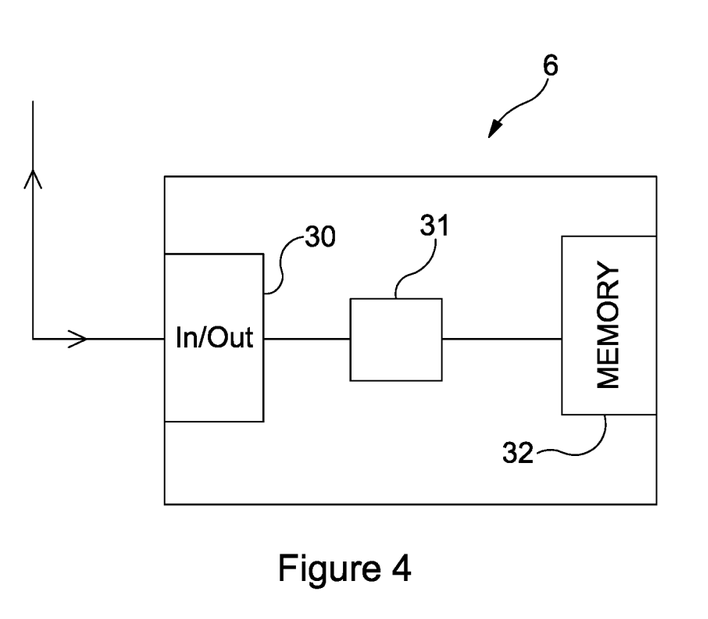
FIG. 4 is a representation of a computer device for use with the system of FIG. 3.

With further reference now to FIG. 4, the controller device 6 is shown in further detail. As can be seen, the controller has an In/Out device 30, a microprocessor 31 and a memory 32. The memory may be used to store a control computer program for controlling the power supply, and the microprocessor may be used for executing the program. The program has instructions which, when executed by the processor, generates a control signal for sending to the power supply. The control signal includes information for the power supply to provide the necessary electrical current to the motor to achieve the desired speed.

The In/Out device 30 is used for sending the control signal. The In/Out device 30 is also used for receiving the electrical parameter data from the current measurement device 8 and also for receiving speed data. The processor 31 is used to process the received data. The memory 32 may be used to store desired compressor speed or compression level data, for example, a set desired speed for the compressor, or a desired speed program for the compressor, e.g. speed ramp up program comprising desired speed with respect to time. The processor may operate to perform a comparison of the speed data with the reference data or set speed, in order to determine whether to increase or decrease the current. This comparison may be performed according to the computer program. The memory may further store an analysis computer program comprising instructions for analysing the electrical parameter data. The processor may execute the analysis program to estimate the fluid property from the electrical parameter data, for example by multiplying the electrical parameter data with a pre-determined correlator to obtain the property of the fluid flow.

In other embodiments, the apparatus may be provided with a computer device, which may comprise the controller 6 or components thereof. In one example, the computer device includes the controller 6 and a display. The data received, processed and/or analysed data by the controller may be displayed on the display for analysis by a user. In some variants, the computer apparatus or controller or components thereof may be distributed, and in communication over a network. Thus, the connecting lines between components 30, 31 and 32 shown in FIG. 4 may be considered communication links. In other embodiments, the controller 6 may be provided as an individual unit.

As has been proposed, by sampling the standard deviation of the supply current to the motor, inferences can be made about the phase composition of the fluid. Referring again to FIG. 5, this shows the effects of increasing the proportion of liquid in a fluid flow through the compressor. The relatively thin line (more stable and commencing at "0" on the Time axis) indicates the amount of liquid injected measured by a reference source. Injection of fluid is performed stepwise at times indicated by step changes in line. The current supplied to maintain a constant compressor speed is shown by the relatively thick line (highly varying and starting at approximately "16:00 on the Time axis). Not only is there an increase in the current, but the deviation shown by the thin line, e.g. the standard deviation, of the measured supply current increases. Accordingly, large observed deviations in the measured current can indicate a large amount of liquid. The deviation is an additional parameter which can be used together with the current to diagnose problems. For example, if the current is increased but the deviation is not, then it could be possible to conclude that the current increase is not due to the liquid content in the flow, but has other origins. For example it may indicate wear in the compressor components.

Figure 5:
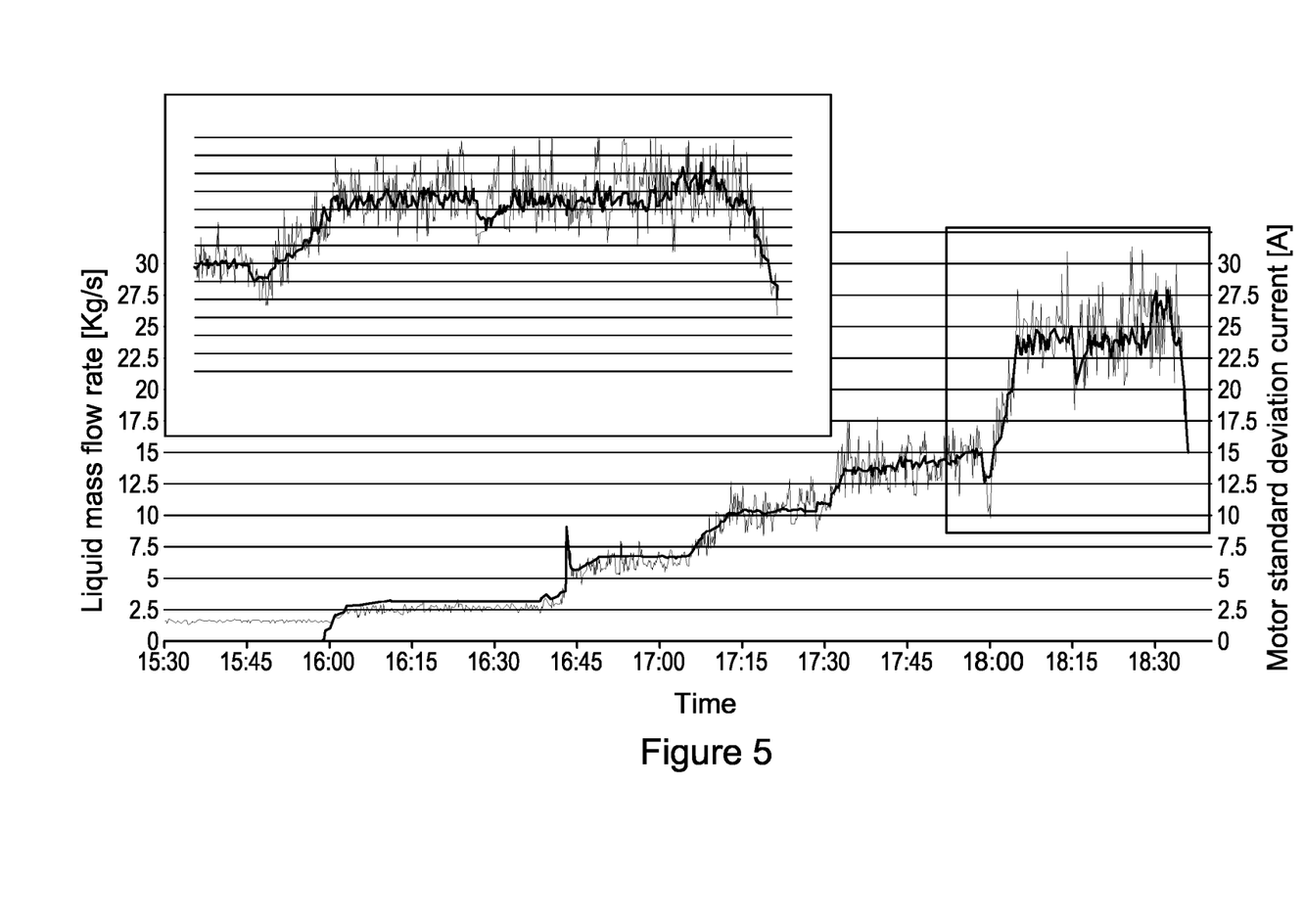
FIG. 5 illustrates measured motor current fluctuations (right axis) versus time, plotted together with an actual liquid injection mass flow rate (left axis)

It should be noted that with reference to FIG. 5, in the example considered, the motor standard deviation current (A) matches to the liquid mass flow rate (Kg/s). This results however from the particular example considered. For other machines it may be necessary to add a constant to the motor standard deviation current, and calibrate the measured data using previously observed results.

By employing the novel and inventive approach described here, it may be possible to eliminate the need for multiphase flow meters to determine the phase composition or liquid content in the fluid flow. If used together with a flow meter, the current data can be a diagnostic indicator for the compressor. Thus, for example, if the current and the deviation increase with increasing liquid measured by the flow meter, then it may be determined that the compressor is operating effectively. If not, then it may be determined that the compressor is not operating effectively.

Figure 6:
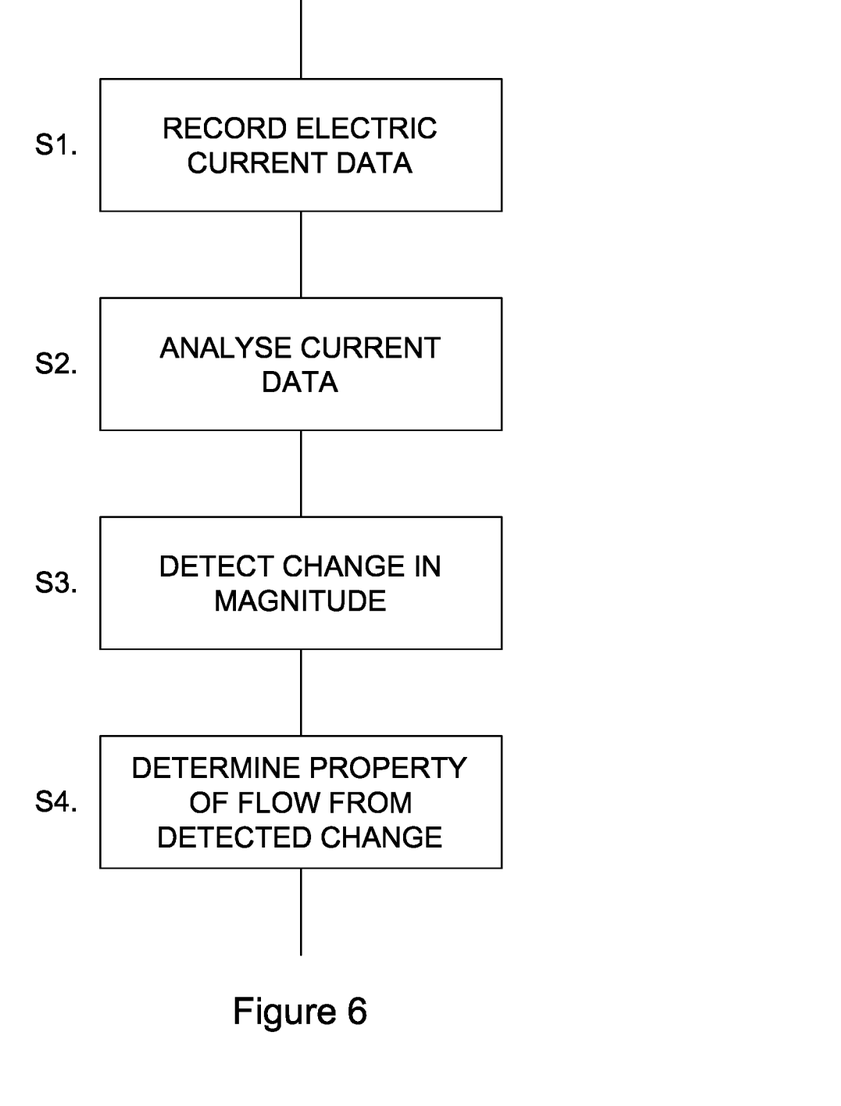
FIG. 6 is a flow diagram illustrating a method of determining changes in the phase composition of a fluid flow through a compressor.

In FIG. 6, an example method of determining a property of the fluid flow is shown, having the steps S1 to S4 wherein:

S1. The electric current supplied to the compressor is recorded. The compressor may be configured to be operated with constant speed in the presence of varying flow.

S2 & S3. The recorded current data are analysed and changes in magnitude of the current are found.

S4. The changes in magnitude are used to indicate a property of the flow through the compressor. For example, a reduction in liquid content can be determined.

In some scenarios it may be helpful to include a pipe segment geometry or equipment upstream of the machine in order to induce certain transient behaviour of the fluid phase that we want to detect. For example, in the case of the unwanted presence of a second phase (gas in a liquid system), this geometry or equipment may cause the unwanted phase to adopt a different flow pattern. With reference to FIG. 1, the flow pattern will be moved to conform to a different segment of the diagram.

A potential enhancement to the methodology described above by taking into consideration that, where the primary phase is gas, the presence of liquid in the compressor is likely to cool the gas during the compression process. For an inlet temperature of 15° C., in the absence of liquid phase the outlet temperature may be expected to be around 100° C. In the presence of a liquid, the outlet temperature may be reduced to 92° C. or even lower due to evaporation of the condensate/oil. However, the degree to which the outlet temperature is reduced will depend upon the nature of the liquid phase. Oil will contribute much more to cool the gas during the compression process since it will partially evaporate, while the presence of water (and or MEG (glycol) will produce only minimal cooling (some additional cooling will be effected by the gas due to the higher temperature but not to the same extent as will result from the presence of condensate/oil). By measuring the pressure and temperature at the inlet and the outlet of the machine, the actual cooling effect (removed energy) provided by the liquids can be determined. By comparing this in turn with the removed energy from a normally dry compression process, the liquid composition at the inlet may be estimated, i.e. how much is water/glycol compared to the oil/condensate.

It will be appreciated by the person of skill in the art that various modifications may be made to the embodiments described above without departing from the scope of the invention. For example, the monitored data may be useful in diagnosing faults with the turbomachine. If a change in the monitored data cannot be correlated with a change in the phase composition of a fluid, this might be indicative of a fault, and can be flagged to an operator and/or used to control the turbomachine.

The methodology has been illustrated above with reference to a frequency driven motor-compressor. However, the methodology is relevant for other types of machinery facing a mixture of gas and liquid where signals are available to determine the compositional fluid data in a similar way. For example, the methodology is applicable to machines in which a gear box is used to transfer rotational power from the motor. The methodology is also applicable to machines where the compressor, pump or the like is not driven directly by a motor but a turbine (for example).

The invention claimed is:

1. A method of identifying the changes in the mass flow rate of a fluid flowing into a turbomachine comprising a motor, the method comprising the steps of:
monitoring changes in at least one electrical parameter of an electrical power supply used to drive a motor of the turbomachine;
associating the monitored changes in said at least one electrical parameter with an actual mass flow rate of the fluid into the turbomachine based on a predetermined correlation between mass flow rate changes and changes in said at least one electrical parameter obtained from a calibration procedure, wherein the at least one electrical parameter comprises current of the motor and the calibration procedure comprises adding a constant to standard deviation of the current;
determining a property of the fluid flowing into the turbomachine according to the association of the monitored changes with changes in the actual mass flow rate of the fluid into the turbomachine; and
controlling an operation of the turbomachine according to the determined property of the fluid flowing into the turbomachine.

2. The method according to claim 1, wherein said turbomachine comprises a turbine, a compressor or a pump.

3. The method according to claim 1, wherein said at least one electrical parameter comprises at least one of a current, voltage or power of the electrical power supply.

4. The method according to claim 3, wherein said electrical power supply is controlled by a frequency converter or a fixed power grid frequency.

5. The method according to claim 4, further comprising the step of configuring said frequency converter or a fixed power grid frequency to maintain a substantially constant motor speed or fluid compression level.

6. The method according to claim 1, where said at least one electrical parameter comprises a parameter of a control signal used to stabilise the turbomachine.

7. The method according to claim 1, wherein said step of monitoring changes in at least one electrical parameter associated with operation of the turbomachine comprises monitoring changes in the absolute value of said parameter.

8. The method according to claim 1, wherein said step of monitoring changes in at least one electrical parameter associated with operation of the turbomachine comprises monitoring changes in a standard deviation of the parameter.

9. The method according to claim 8, further comprising the step of sampling the deviation of one of said at least one electrical parameter at each of successive sampling windows.

10. The method according to claim 1, wherein said changes in the mass flow rate result from changes in the liquid fraction of a fluid containing liquid and gas.

11. The method according to claim 1, wherein said fluid comprises hydrocarbons flowing from a production well.

12. The method according to claim 11, wherein said turbomachine is provided at a subsea location.

13. The method according to claim 1, further comprising the step of controlling a valve associated with the turbomachine.

14. The method according to claim 13, wherein said valve is an anti-surge valve.

15. A system comprising a monitor for monitoring changes in the mass flow rate of a fluid flowing into a turbomachine comprising a motor, the monitor comprising:

a detector for monitoring changes in at least one electrical parameter associated with a turbine, compression or pump operation of a turbomachine; and an analyser for associating the monitored changes in said at least one electrical parameter with an actual mass flow rate of the fluid into the turbomachine based on a predetermined correlation between mass flow rate changes and changes in said at least one electrical parameter obtained from a calibration procedure, wherein the at least one electrical parameter comprises current of the motor and the calibration procedure comprises adding a constant to standard deviation of the current, wherein the system further comprises a controller that controls the operation of the turbomachine based on the actual mass flow rate associated by the analyser.

16. The monitor according to claim 15, wherein said detector comprises one of a current, voltage or power meter.

17. The monitor according to claim 16, where said detector is configured to be coupled to an electrical power supply line used to drive a motor of the turbomachine.

18. The monitor according to claim 15, wherein said detector is configured to monitor changes in at least one electrical parameter associated with operation of the turbomachine by monitoring changes in a standard deviation of the parameter.

19. A computer program embodied on a non-transitory computer readable medium, the computer program, when run on a computer, causes the computer to:

monitor changes in at least one electrical parameter associated with a turbomachine comprising a motor;

associate the monitored changes in said at least one electrical parameter with an actual mass flow rate of the fluid into the turbomachine based on a predetermined correlation between mass flow rate changes and changes in said at least one electrical parameter obtained from a calibration procedure, wherein the at least one electrical parameter comprises current of the motor and the calibration procedure comprises adding a constant to standard deviation of the current;

determine a property of the fluid flowing into the turbomachine according to the association of the monitored changes with changes in the actual mass flow rate of the fluid into the turbomachine; and control an operation of the turbomachine according to the determined property of the fluid flowing into the turbomachine.

* * * * *